United States Patent [19]

Zierenberg et al.

[11] Patent Number: 5,112,842

[45] Date of Patent: May 12, 1992

[54] TRANSDERMAL ADMINISTRATION OF 2-AMINO-6-N-PROPYLAMINO-4,5,6,7-TETRAHYDROBENZOTHIAZOLE

[75] Inventors: Bernd Zierenberg, Bingen; Michael Herschel, Kastrich; Uwe Rohr, Kreuzweg, all of Fed. Rep. of Germany

[73] Assignee: Boehringer Ingelheim KG, Ingelheim am Rhein, Fed. Rep. of Germany

[21] Appl. No.: 610,870

[22] Filed: Nov. 8, 1990

[30] Foreign Application Priority Data

Nov. 9, 1989 [DE] Fed. Rep. of Germany ....... 3937271

[51] Int. Cl.⁵ .......................................... A61K 31/425
[52] U.S. Cl. .......................................................... 514/367
[58] Field of Search ......................................... 514/367

*Primary Examiner*—S. J. Friedman
*Attorney, Agent, or Firm*—David E. Frankhouse; Daniel Reitenbach; Mary-Ellen M. Timbers

[57] ABSTRACT

The invention relates to the transdermal administration of 2-amino-6-n-propylamino-4,5,6,7-tetrahydrobenzothiazole or the (—)-enantiomer thereof and transdermal systems containing these active substances.

9 Claims, 1 Drawing Sheet

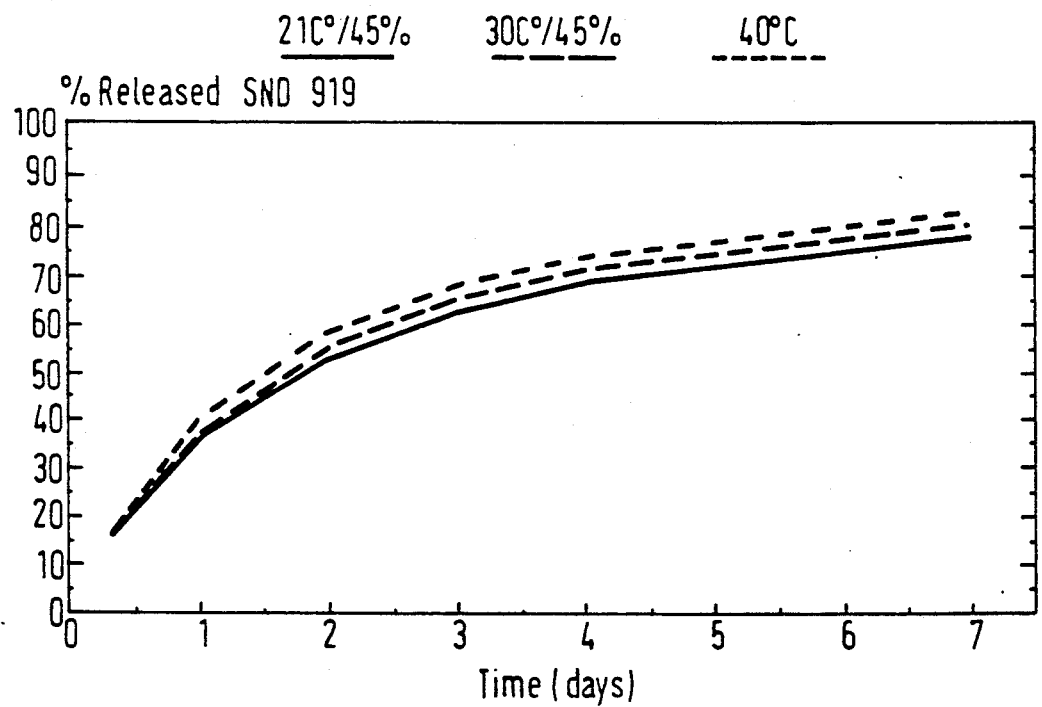
FIG.1 In vitro release of SND 919.

TRANSDERMAL ADMINISTRATION OF 2-AMINO-6-N-PROPYLAMINO-4,5,6,7-TETRAHYDROBENZOTHIAZOLE

The present invention relates to the transdermal administration of 2-amino-6-n-propylamino-4,5,6,7-tetrahydrobenzothiazole, particularly the (−)-enantiomer thereof and the pharmacologically acceptable acid addition salts thereof.

The above-mentioned compounds are known as drugs, primarily for the treatment of schizophrenia and Parkinsonism or Parkinson's disease. Details of the preparation of these compounds can be found in European Patent Application, EP-A- 85 116 016. It has now been found that conventional galenic preparations as proposed hitherto are not suitable for making the active substance available to the patient in a satisfactory manner. Even at doses of 100 to 200 µg per day, orthostatic side effects have been observed in patients. Previous findings indicate that single doses of between 50 and 300 µg are required in order to achieve a pharmacological effect, whilst the total daily dose is correspondingly higher.

The aim of the present invention is to provide a method by which 2-amino-6-n-propylamino-4,5,6,7-tetrahydrobenzothiazole and the (−)-enantiomer thereof can be administered in doses of >200 µg per day without producing orthostatic side effects in the patient.

Surprisingly, this objective is achieved by transdermal administration of the active substance. It has been found that, by transdermal administration of Pramipexole (SND 919, Pramipexole), doses of 2 mg per day can be administered without any orthostatic side effects occurring in the patient. This corresponds to 10 times the amount which can usually be administered by oral application of the substance (200 µg per day) without orthostatic side effects. The present invention further relates to transdermal therapeutic systems which contain as active substance 2-amino-6-n-propylamino- 4,5,6,7-tetrahydrobenzothiazole or the (−)-enantiomer thereof (SND 919, Pramipexole). The nature and structure of the transdermal therapeutic system should not be regarded as critical, provided that the excipients and carriers used are compatible with the active substances described according to the invention and the active substance is released in a quantity sufficient to achieve the desired therapeutic effect.

Systems suitable for transdermal administration are known from the prior art. Thus, for example, U.S. Pat. No. 3,558,122 discloses a transdermally therapeutic system comprising a backing layer which is impervious to the active substance, a reservoir of active substance and means for fixing the system to the skin. This system may contain special devices, e.g. a membrane, for controlling the release of active substance. A method of producing a transdermal system in the form of a polyacrylate film is known from European Patent 86 997. In another embodiment according to the invention, the active substance may also be administered by means of an iontophoretic system. Systems of this kind are described, for example, in European Patent Applications 60 452, 178 601, 147 524, 182 765 and in German Offenlegungsschrift 32 25 748. Although the solution to the present problem is not limited to the use of a specific system—provided that the system ensures an adequate release of active substance—systems which have an active substance reservoir consisting of an emulsion polymerised polyacrylate are preferred according to the invention. Such systems are known, for example, from European Patent Specifications 20 905, 86 997 and European Patent Application 209 121, the contents of which are hereby drawn to the reader's attention. Using the systems described in these patents it is possible to administer 2-amino-6-n-propylamino-4,5,6,7-tetrahydrobenzothiazole or the (−)-enantiomer thereof (SND 919) in a dose of 0.5 to 5 mg per day without any orthostatic side effects being observed.

In a preferred embodiment, the system according to the invention consists of a backing layer which is impervious to the active substance and is simultaneously formed as a covering plaster to secure the system to the skin, a reservoir containing the active substance and a removable protective film which protects the system before it is ready to be used. The preferred carrier material polyacrylate of the type marketed as Eudragit NE 30 D$^R$ by Röhm GmbH of Darmstadt. The proportion of active substance in this reservoir is between 5 and 30% by weight, the preferred range being between 7 and 15% by weight.

The following Examples illustrate the invention in a non-restrictive manner.

For the Examples, Eudragit E 30 D made by Röhm of Darmstadt was used as the polyacrylate.

EXAMPLE 1

Active substance Pramipexole (SND 919)

a) Solvent acetone 8 g of freeze-dried polyacrylate, 2 g of Pramipexole and 91 g of acetone were placed in a suitable container and stirred for about 12 hours with a magnetic stirrer until a homogeneous, relatively viscous solution was obtained. This solution was then poured into casting moulds in amounts of 190 mg/cm$^2$. At ambient temperature the solvent acetone evaporated after about 6 hours. A smooth film was obtained, containing 8.4 mg of polyacrylate and 2 mg of Pramipexole per cm$^2$.

b) Solvent ethyl acetate

The starting solution had the following composition: 6 g of polyacrylate, 1.06 g Pramipexole and 93.5 g of ethyl acetate. When applied in amounts of 390 mg/cm$^2$ this produced a film containing 2 mg of Pramipexole and 11.6 mg of polyacrylate per cm$^2$.

c) Solvent methylene chloride

The starting solution contained: 3 g of polyacrylate, 0.74 g Pramipexole and 96.6 g of methylene chloride. When applied in amounts of 650 mg/cm$^2$, after drying a film was obtained containing 2 mg of Pramipexole and 9.64 mg of polyacrylate per cm$^2$.

The following plaster was produced analogously to the method described above:

| Reservoir: | |
| --- | --- |
| Material | Eudragit NE 30 D ® |
| Surface area | 20 cm$^2$ |
| Thickness | 200 µm |
| Content of active substance | 9% by wt. = 43.3 mg SND 919 |

Rates of release of SND 919 in vivo:

The plaster described above was fixed to the arm of two test subjects for 3 and 4 days, respectively, under medically reproducible conditions. The dosage used was about 2.5 mg per day for each test subject. The blood levels measured are shown in Table A. These measurements were obtained by Radio Immune Assay (RIA).

TABLE A

Concentration of SND 919 in the blood after administration of a CPA-plaster charged with 9.0% by weight of SND 919: size 20 cm$^2$

|  | Day | Time | SND 919 ng/ml |
|---|---|---|---|
| Subject A | 3rd day | 8:30 | 0.57 |
|  | 4th day | 8:30 | 1:54 |
| Subject B | 3rd day | 8:30 | 0.88 |
|  | 3rd day | 12:00 | 1.48 |
|  | 3rd day | 15:00 | 1.31 |

FIG. I shows the in vitro release of SND 919 from a Eudragit NE 30 D polyacrylate plaster.

| Area of plaster | 20 cm$^2$ |
|---|---|
| Quantity of active substance | 43.3 mg = 9% |
| Thickness | 200 μm |

The measurements were obtained using the USP 21, eighth edition.

What is claimed is:

1. A method for attenuating the orthostatic side effects of administration of 2-amino-6-n-propylamino-4,5,6,7-tetrahydrobenzothiazole or the (−)-enantiomer thereof, in a patient, which comprises administering the 2-amino-6-n-propylamino-4,5,6,7-tetrahydrobenzothiazole or the (−)-enantiomer thereof, to the patient transdermally.

2. A method as recited in claim 1 wherein the dosage of 2-amino-6-n-propylamino-4,5,6,7-tetrahydrobenzothiazole or the (−)-enantiomer thereof, administered to the patient is greater than 200 μg per day.

3. A method as recited in claim 1 wherein the dosage is between about 0.5 mg to about 5 mg per day.

4. A method for treating a patient suffering from schizophrenia which comprises transdermally administering to the patient an effective dosage of 2-amino-6-n-propylamino-4,5,6,7-tetrahydrobenzothiazole or the (−)-enantiomer thereof.

5. A method as recited in claim 4 wherein the effective dosage is greater than 200 μg per day.

6. A method as recited in claim 5 wherein the effective dosage is between about 0.5 mg to about 5 mg per day.

7. A method for treating a patient suffering from Parkinson's Disease which comprises transdermally administering to the patient an effective dosage of 2-amino-6-n-propylamino-4,5,6,7-tetrahydrobenzothiazole or the (−)-enantiomer thereof.

8. A method as recited in claim 7 wherein the effective dosage is greater than 200 μg per day.

9. A method as recited in claim 8 wherein the effective dosage is between about 0.5 mg to about 5 mg per day.

* * * * *